United States Patent [19]

Felts et al.

[11] 4,178,285

[45] Dec. 11, 1979

[54] SEPARATION OF ACTIVE $\alpha_1$-ACID GLYCOPROTEIN AND UTILIZATION IN THE LIPOPROTEIN LIPASE ENZYME SYSTEM

[76] Inventors: James M. Felts, 2299 Pacific Ave. #62, San Francisco, Calif. 94115; Ilona Staprans, 2052 20th St., San Francisco, Calif. 94117

[21] Appl. No.: 971,484

[22] Filed: Dec. 20, 1978

[51] Int. Cl.$^2$ .................... C07G 7/00; C07G 15/00
[52] U.S. Cl. ................... 260/112 R; 424/99; 424/100; 424/177
[58] Field of Search ............. 260/112 R; 424/99, 100, 424/177

[56] References Cited

U.S. PATENT DOCUMENTS

| | | | |
|---|---|---|---|
| 2,001,255 | 5/1935 | Langecker | 424/100 X |
| 3,703,591 | 11/1972 | Bucolo | 195/103.5 R |
| 3,759,793 | 9/1973 | Stork et al. | 195/103.5 R |
| 3,862,009 | 1/1975 | Wattlefeld et al. | 195/103.5 R |
| 3,898,130 | 8/1975 | Komatsu | 195/103.5 R X |
| 3,901,763 | 8/1975 | Horiuchi et al. | 195/66 R |
| 4,056,442 | 11/1977 | Huang et al. | 424/2 X |

OTHER PUBLICATIONS

The Physiologist, vol. 20, No. 4, Aug. 1977.
Circulation, 56(4), III-245, 1977, Staprans et al.
Biochem. Biophys. Res. Comm., 79(4):1272-1278 (1977), Staprans et al. Dec. 21, 1977.
Clin. Chim. Acta, 6:503-507 (1961), Hardwicke et al.

Primary Examiner—Howard E. Schain
Attorney, Agent, or Firm—John S. Roberts, Jr.

[57] ABSTRACT

This invention relates to a method of separating the active $\alpha_1$-acid glycoprotein fraction, a co-factor in the lipoprotein lipase reaction, from urine of nephrotic animals and humans as follows:

(a) concentrate the said urine to about 10-20% by volume;

(b) precipitate undesired protein at pH 4 with ammonium sulfate; and (c) recover the $\alpha_1$-acid glycoprotein fraction from the supernatant, neutralize with solid NaHCO$_3$, and purify by dialysis versus H$_2$O and lyophilize.

This active $\alpha_1$-acid glycoprotein fraction is utilized in effective amounts in nephrotic animals to reverse the defect in triglyceride removal caused by the loss of plasma constituents in urine.

4 Claims, 1 Drawing Figure

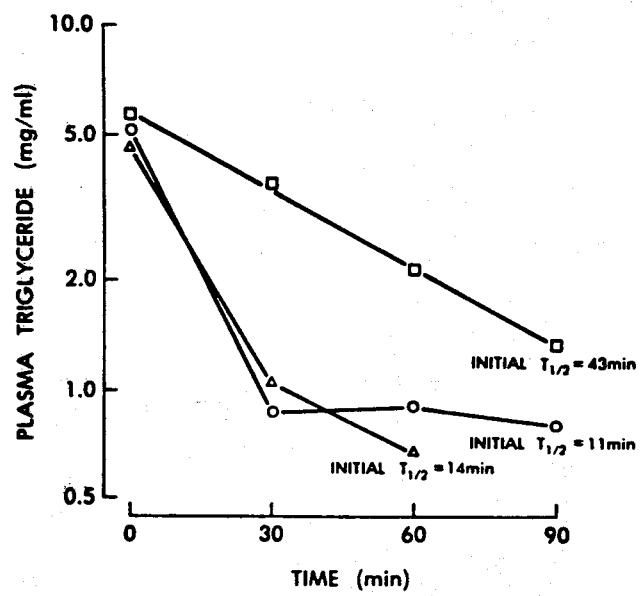
The rate of TG clearance in 4 normal (Δ), 2 nephrotic (□) and 3 $\alpha_1$-AG-treated nephrotic (o) rats. Points represent average values for each group.

SEPARATION OF ACTIVE $\alpha_1$-ACID GLYCOPROTEIN AND UTILIZATION IN THE LIPOPROTEIN LIPASE ENZYME SYSTEM The invention described herein was made in the course of work under a grant or award from the Department of Health, Education, and Welfare.

The present invention has as one target a new method of separating the active $\alpha_1$-acid glycoprotein ($\alpha_1$-AG) fraction, which is a co-factor in the lipoprotein lipase reaction, from nephrotic animal and human urine. This method of separation is as follows:

(a) concentrate the urine to about 10–20% by volume;

(b) precipitate undesired protein at pH 4 with ammonium sulfate;

(c) recover the $\alpha_1$-acid glycoprotein from the supernatant, neutralize with solid $NaHCO_3$, and purify by dialysis versus $H_2O$ and lyophilize.

This active $\alpha_1$-AG fraction is utilized in effective amounts in nephrotic animals to reverse the defect in triglyceride removal caused by the loss of plasma constituents in urine.

It was found that the activity of the $\alpha_1$-AG fraction depended also upon the presence of C-II apolipoprotein which is a protein moiety of plasma lipoproteins which binds the lipid moiety to form the hololipoprotein. The enzymatic fracturers of lipids by lipase is, of course, known and examples in the art are as follows:

U.S. Pat. No. 3,703,591 Bucolo et al
U.S. Pat. No. 3,759,793 Stork et al
U.S. Pat. No. 3,862,009 Wahlefeld et al
U.S. Pat. No. 3,898,130 Komatsu
U.S. Pat. No. 3,901,763 Horiuchi et al
U.S. Pat. No. 4,056,442 Huang et al Felts et al, *The Physiologist*, Vol. 20, No. 4, August 1977.

Staprans et al, *Circulation*, 56(4), III-245, 1977.

Staprans et al, *Biochem. Biophys. Res. Comm.*, 79(4):1272–1278 (1977).

The production of an active fraction (active $\alpha AG$) from the protein present in animal and human urine and blood which affects lipolysis and can be used for replacement therapy is not known but is suggested and introduced in the present invention.

Recent experimental work has indicated that the active $\alpha_1$-AG fraction is actually a complex in which there is an active component or moiety and an inactive component or moiety.

BRIEF DESCRIPTION OF THE DRAWING

The FIGURE shows triglyceride clearance in time with fasted rats injected with 50 mg of Intralipid.

BACKGROUND OF THE INVENTION

In the development of this invention there was sought for and found in nephrotic patients the different proteins, lipoproteins and co-factors lost from plasma into urine that might have a regulatory effect on the enzyme system (lipoprotein lipase) that is responsible for clearing fat from the blood. This component or co-factor was identified as a constituent of plasma and as the $\alpha_1$-acid glycoprotein fraction which had a function which was previously unknown.

The problem and its solution in summary is as follows:

Utilizing the active $\alpha_1$-AG produced by the above method, it is used as a new co-factor in the lipoprotein lipase reaction. There was isolated an active form of the compound from nephrotic urine that is effective both in vitro and in vivo. The active $\alpha_1$-AG fraction increased lipolysis 100% in the presence of C-II apolipoprotein in a lipoprotein lipase assay system. Rats with induced nephrotic syndrome showed a decrease in triglyceride clearance. Half time was increased from 15 minutes to 43 minutes. The injection of the $\alpha_1$-AG fraction restored the lipid clearance to normal. These findings suggest that elevated plasma triglycerides in human nephrotic patients are the direct result of excessive loss of $\alpha_1$-AF and/or associated components from plasma into urine and the patients are amenable to replacement therapy.

NEPHROTIC SYNDROME OR KIDNEY DISEASE

A severe excess of lipids in the blood has long been recognized as a common disorder in patients or experimental animals with the kidney disease characterized by excess of protein in urine (proteinuria) and decrease of protein in the blood (hypoproteinemia). It has been estimated that this type of excess of lipids in the blood is associated with an increase in the incidence of ischemic heart disease from 48–85 times that of the general population of the same age. The elevated excess of triglycerides in the blood is considered to result from a slower clearance of chylomicrons and very low density lipoproteins (VLDL) from the circulation, an increased synthesis of VLDL by the liver, or both.

It has been postulated that urinary loss of apolipoproteins and other co-factors necessary for the clearance of triglycerides (TG) by the lipoprotein lipase (LPL) enzyme system is believed responsible for a defective clearance of chylomicrons and VLDL. In the present invention there has been identified an LPL co-factor in urine which is similar or identical to plasma $\alpha_1$-AG and/or an associated component. In experimental nephrotic rats with a TG removal defect, this invention has shown that the $\alpha_1$-AG fraction can restore the rate of TG metabolism to normal.

THE IDENTIFICATION OF $\alpha_1$-ACID GLYCOPROTEIN IN URINE FROM NEPHROTIC PATIENTS A protein common to all urine samples from nephrotic patients was isolated in pure form by preparative polyacrylamide electrophoresis. It was identified as human plasma $\alpha_1$-AG by the amino acid composition which was similar to known values [Marshall, *J. Biol. Chem.*, 241:4731–4737 (1966)]. In addition, the antibody against human plasma $\alpha_1$-AG gave a precipitin band against a purified preparation and not against human serum albumin. Sodium dodecylsulfate (SDS) gel electrophoresis yielded a molecular weight of 45,000 D which is in agreement with the established values for $\alpha_1$-AG of plasma [Li et al, *J. Biol. Chem.*, 243:825–832 (1970)]. The mobility of the urinary protein in basic polyacrylamide gel electrophoresis [Bamburg, et al, *Neurobiology*, 3:162–175 (1973)] was similar to a commercial preparation of purified $\alpha_1$-AG (Miles Laboratories, Inc., Kankakee, Ill.).

THE ACTIVATION OF LIPOPROTEIN LIPASE BY THE $\alpha_1$-AG FRACTION IN VITRO AND THE NECESSITY OF APOLIPOPROTEIN C-II Table I shows the effect of the $\alpha_1$-AG fraction from nephrotic urine on the activity of LPL in the presence and absence of apolipoprotein C-II. If $\alpha_1$-AG was added to the assay in the absence of apolipoprotein C-II, $\alpha_1$-AG had no effect on the enzyme activity. However, when $\alpha_1$-AG was added together with apolipoprotein C-II, LPL enzyme activity increased over 100%. These results show that the $\alpha_1$-AG fraction, in the presence of apolipoprotein C-II, increases the rate of the enzyme reaction.

TABLE I

The Effect of the $\alpha_1$-AG fraction on Lipoprotein Lipase Activity in the In Vitro Assay

| Assay Mixture | FFA Released μmoles/hr |
|---|---|
| LPL (from raw milk) | 0.03 |
| LPL + C-II (3μg) | 1.14 |
| LPL + C-II (3μg) + $\alpha_1$-AG (50μg) | 2.52 |
| LPL + $\alpha_1$-AG (50 μg) | 0.03 |
| LPL + C-II (3μg) + AT (50μg)* | 1.14 |

*AT = antitrypsin, a plasma glycoprotein with a molecular weight, carbohydrate content and charge similar to $\alpha_1$-AG.

SEPARATION OF ACTIVITY FROM THE ACTIVE αAG FRACTION

The "active" component can be separated from the αAG by ion exchange chromatography. The αAG does not adhere to DEAE-cellulose in 0.15 M NaCl and all protein is eluted when the column is washed with 0.15 M NaCl. The "activity" can be removed from the cellulose by increasing the salt concentration of the eluant to 0.8 M NaCl. Thus, by using an anionic exchanger, "activity" can be isolated free from αAG.

IDENTIFICATION OF ACTIVE COMPONENT OF THE ACTIVE αAG COMPLEX AS A GLYCOSAMINOGLYCAN (GAG)

Preliminary evidence indicated that the active component was glycosaminoglycan (GAG) as follows:

(1) The active fraction contained glucuronic acid which is a major component of all GAGs. Activity and glucuronic acid content coincide by gel filtration of the purified component (free of αAG) when carried out in water or guanidine HCl solution.

(2) Activity separated by DEAE-cellulose did not have UV absorption at 280 nm indicating the absence of protein.

(3) Activity was precipitated from the active αAG complex by lysozyme, a protein which has a selective action in precipitating high molecular weight anionic materials such as GAG (Badin et al., *J. Clin. Invest.*, 34:1317, 1955).

(4) The active component stained with Toluidine Blue, which is characteristic of GAGs.

Evidence additionally points to the fact that the active GAG associated with $\alpha_1$-AG is not heparin:

(1) Molecular weight from gel filtration data (in the presence of guanidine HCl) for the active component appears to be in the vicinity of 60,000 D, which is far higher than expected for heparin (8,000 to 20,000 D).

(2) Chromatography on DEAE-Sephadex shows that, unlike heparin, activity is eluted below 1 M NaCl. This is suggestive evidence that the active component may belong to a group of compounds called hyaluronic acids. (Schmidt, *Biochim. Biophys. Acta*, 63:346, 1962).

EXAMPLE 1

Preparation of the active $\alpha_1$-Acid Glycoprotein Fraction $\alpha_1$-AG preparation was based on a method described by Hardwicke et al, *Clin. Chim. Acta*, 6:503–507 (1961). Urine from patients with nephrotic syndrome was used as a source of the $\alpha_1$-AG (orosomucoid) fraction. Urine was concentrated to about 10–20% of the original volume using a Millipore Pellicon membrane. The major portion of the protein was precipitated at 50% saturation (36 g/100 ml) with ammonium sulfate at pH 4.0. The precipitate was removed by centrifugation and the supernatant containing the $\alpha_1$-AG fraction was immediately neutralized with solid NaHCO$_3$. Long exposure of the protein to low pH yielded an inactive product. All procedures were performed in ice. The supernatant was then dialyzed extensively against water in the cold (0–4°) and concentrated in an Amicon Filtration Cell using a UM20 membrane. Alternatively, the supernatant was dialyzed against distilled H$_2$O and then lyophilized. For final purification of the $\alpha_1$-AG, the last traces of contaminating albumin and other proteins were removed by Affi-Gel Blue (Bio-Rad Laboratories) affinity chromatography. This isolation technique can also be applied to plasma, peritoneal fluid and other sources of the $\alpha_1$-AG fraction.

Where intended for amino acid analysis, $\alpha_1$-AG was isolated in pure form by preparative polyacrylamide gel electrophoresis, with a preparative gel system (Savant Instruments, Inc., Hicksville, NY).

Amino acid analysis was performed according to Spackman et al, *Anal. Chem.*, 30:1190–1206 (1958). Protein was hydrolized in vacuo for 22 hr in the presence of constant boiling HCl.

Sodium dodecylsulfate gel electrophoresis (SDS) was performed according to Weber and Osborn, *J. Biol. Chem.*, 244:4406–4412 (1969).

Apolipoprotein C-II (R-glutamic acid) for lipoprotein lipase activation in the in vitro assay was prepared from VLDL as described by Herbert et al, *J. Biol. Chem.*, 248:4941–4946 (1973). VLDL was isolated from outdated plasma by ultracentrifugation at a density of 1.030 and delipidated by butanol-isopropyl ether. VLDL apoprotein was first chromatographed on Sephacryl S-200 (Pharmacia) and then on DEAE-cellulose using 6 M urea in the eluting buffers. Purified apolipoprotein C-II was dialyzed against 0.15 M NaCl, 0.02 M Tris-CHl, pH 8.0 and used as an activator in the LPL assay.

Lipoprotein lipase was prepared from fresh unpasteurized skim milk using methods described by Olivecrona et al, *Biochem. Biophys. Res. Commun.*, 43:524–529 (1971). Final purification was carried out on a heparin-Sepharose column. The eluted active fraction was used as "purified" enzyme in the assay mixture.

EXAMPLE 2

In Vitro Studies of LPL Activity

The assay was based on the procedure described by Felts, et al, *Biochem. Biophys. Res. Commun.*, 66:1467–1475 (1975). A 1.0 ml reaction mixture consisted of 0.1 ml 1.3 M Tris-HCl, pH 8.6; 0.1 ml 0.02 M CaCl$_2$; 0.3 ml BSA, 15.0%; 0.1 ml of Intralipid (10%, Vitrum, Stockholm, Sweden); 0.03 ml apolipoprotein C-II, 100 μg/ml; 0.10 ml enzyme; 0.27 ml was allowed for additional variables ($\alpha_1$-AG fraction) or water. Duplicate samples were incubated for 60 min. at 37° C. and the free fatty acid (FFA) content was determined by titration. A reaction mixture lacking the apolipoprotein C-II activator was incubated under the same conditions as a control blank. Enzyme activity was calculated as μmoles FFA released per hour.

EXAMPLE 3

Effect of the $\alpha_1$-AG fraction on Triglyceride Clearance in Nephrotic Rats in Vivo Experimental nephrosis was induced in rats by injecting puromycin aminoucleoside. Table 2 shows that the puromycin injected rats displayed the common disorders of human nephrotic syndrome: proteinuria, hypoproteinemia, and hypertriglyeridemia.

TABLE 2

Plasma and Urine Composition of Control and Nephrotic Rats

| Animal Group (n) | Plama Triglycerides | Plasma Proteins | Urine Proteins |
|---|---|---|---|
| | mg/dl | g/dl | mg/24hr |
| Control (4) | 55 ± 9.4* | 7.6 ± 0.24 | trace |
| Nephrotic (5) | 138 ± 39.8 | 4.5 ± 0.11 | 560 ± 149.6 |

*mean ± S.D.

The FIGURE shows the triglyceride clearance in fasted rats injected with 50 mg Intralipid. Nephrotic rats displayed a reduced rate of TG clearance: the initial half time was 43 min. compared to normal rats with an initial half time of 14 min. However, nephrotic rats which were injected with the $\alpha_1$-AG fraction cleared TG with an initial half time of 11 min., which is equivalent to the normal rate. Thus, the injection of the active $\alpha_1$-AG fraction reversed the defective triglyceride clearance mechanism in rats with the nephrotic syndrome. The half times for normal and treated nephrotic rats are approximate, since measurements were not taken earlier than 30 min. C-II apolipoprotein injection was not necessary in nephrotic rats since this co-factor is not limiting in the lipoprotein lipase reaction in vivo.

In vivo experiments with nephrotic rats. Adult (250-300 G) male rats (Long-Evans) were used. In these studies the rats were given Berkeley Diet A and water ad lib. Experimental nephrotic syndrome was induced by nine daily subcutaneous injections of puromycin aminonucleoside (Sigma) at a dose of 1.67 mg/100 g body weight. Urinary protein was monitored for indication of the extent of nephrosis. Two days after the last injection, rats were fasted for 18 hr and their plasma triglycerides determined from blood collected from a tail vein. Half of the nephrotic rats were injected with 0.05 ml Intralipid (50 mg triglycerides) and 0.5 ml $\alpha_1$-AG fraction (25 mg). For control purposes, in the remaining half of the nephrotic rats, $\alpha_1$-AG fraction was replaced with 0.15 M NaCl. After the injection of Intralipid with or without the $\alpha_1$-AG fraction, blood samples from all rats were collected at 30, 60, and 90 min. intervals and plasma triglycerides were determined. Zero-time values were calculated from initial plasma triglycerides plus the amount of Intralipid injected, taking into account the plasma volume (5% body weight).

We claim:

1. A method of separating the active $\alpha_1$-acid glycoprotein fraction, which contains a co-factor in the lipoprotein lipase reaction, from nephrotic urine as follows:
   (a) concentrate the said urine to about 10-20% by volume;
   (b) precipitate undesired protein at pH 4 with ammonium sulfate;
   (c) recover the $\alpha_1$-acid glycoprotein fraction from the supernatant, neutralize with solid NaHCO$_3$, and purify by dialysis versus H$_2$O and lyophilize.

2. The method of claim 1 wherein the $\alpha_1$-acid glycoprotein is recovered in the presence of an active glycosaminoglycan (GAG) with lipoprotein lipase co-factor activity.

3. The method of claim 1 wherein an active complex is produced embodying $\alpha_1$-acid glycoprotein in the presence of GAG, which complex may be further separated into active and inactive components.

4. The method of claim 1 wherein each procedure is performed in the cold at 0°-4° C.

* * * * *